(12) United States Patent
Haj-Yehia

(10) Patent No.: US 6,492,405 B2
(45) Date of Patent: Dec. 10, 2002

(54) NITRIC OXIDE DONORS AND PHARMACEUTICAL COMPOSITIONS CONTAINING THEM

(75) Inventor: Abdullah Haj-Yehia, Jerusalem (IL)

(73) Assignee: Yissum Research Development Company of the Hebrew University of Jerusalem, Jerusalem (IL)

(*) Notice: Subject to any disclaimer, the term of this patent is extended or adjusted under 35 U.S.C. 154(b) by 0 days.

(21) Appl. No.: 10/041,674

(22) Filed: Jan. 9, 2002

(65) Prior Publication Data

US 2002/0161235 A1 Oct. 31, 2002

Related U.S. Application Data

(62) Division of application No. 09/381,303, filed on Dec. 30, 1999, now Pat. No. 6,369,071.

(51) Int. Cl.[7] ............... A61K 31/385; A61K 31/426; C07D 213/71; C07D 277/14; C07D 339/04
(52) U.S. Cl. ............. 514/369; 546/298; 546/299; 546/261; 546/301; 548/200; 549/39; 549/32; 564/300; 568/23; 514/335; 514/348; 514/351; 514/356; 514/365; 514/369; 514/440
(58) Field of Search .................. 546/298, 299, 546/301, 261; 548/200; 549/39, 32; 564/300; 514/335, 347, 348, 350, 351, 356, 365, 369, 440; 568/23

(56) References Cited

PUBLICATIONS

Dhami, Kawal S., Addition products of various halogens and carbomethoxymethyl malonate monothioallylamide, Correction., 1975, Indian J. Chem., 13 (9), 989.*

* cited by examiner

*Primary Examiner*—Alan L. Rotman
*Assistant Examiner*—Janet L Coppins
(74) *Attorney, Agent, or Firm*—Eitan, Pearl, Latzer & Cohen-Zedek

(57) ABSTRACT

The present invention provides a compound containing at least one sulfhydryl group and at least one NO donor group, wherein said compound is a) a compound containing one or more sulfhydryl groups linked to at least one aromatic ring or a heteroaromatic ring with a nitrogen in the ring structure, which ring is substituted by one or more substituents bearing a terminal —$ONO_2$ group; b) a 5-membered ring heterocyclic compound containing a sulfur atom and a nitrogen atom, which ring is substituted by one or more substituents bearing a terminal —$ONO_2$ group; c) a 5-membered ring compound containing two conjugate S-atoms, which ring is linked to one or more substituents bearing a terminal —$ONO_2$ group; or d) a compound containing an acyclic —S—S group, linked to at least one aromatic ring or a heteroaromatic ring with a nitrogen in the ring structure, which ring is substituted by one or more substituents bearing a terminal —$ONO_2$ group. The present invention further provides pharmaceutical compositions comprising one or more of said compounds as an active ingredient.

6 Claims, No Drawings

NITRIC OXIDE DONORS AND PHARMACEUTICAL COMPOSITIONS CONTAINING THEM

CONTINUING APPLICATION DATA

This application is a Divisional Application of U.S. Ser. No. 09/381,303, filed Dec. 30, 1999, now U.S. Pat. No. 6,369,071 incorporated herein by reference.

FIELD OF THE INVENTION

The present invention relates to nitric oxide donors containing at least one sulfhydryl group or a group capable of being converted in-vivo to a sulfhydryl group, and at least one nitric oxide donor group. The novel compounds are effective substitutes for existing tolerance-inducing organic or inorganic nitric oxide donors.

BACKGROUND OF THE INVENTION

For over a century, the nitric oxide (NO) donor nitroglycerin (GTN) has been the mainstay in the treatment of angina and related heart diseases. However, the existing mechanisms proposing the mediation of GTN action by free NO, intracellular or extracellular S-nitrosothiol formation and subsequent activation of guanylyl cyclase (GC), as well as those describing GTN tolerance, have become increasingly controversial. The phenomenon of tolerance to GTN, however, is of special clinical importance. In fact, early tolerance to the anti-anginal effects of the drug is the major drawback of nitrate therapy, especially during acute myocardial infarction. This is particularly important since alternative non-tolerance inducing agents have not yet been developed to successfully replace therapy with GTN.

Based on accumulating evidence, Applicant hypothesized that GTN may directly interact with SH-group/s located on its target enzyme (GC) resulting in its S-nitrosylation and activation. However, subsequent auto-oxidation (disulfide formation) of these SH-groups renders the enzyme inert towards farther reaction with GIN, resulting in tolerance development.

Additionally, evidence has recently been provided to support an involvement of the superoxide anion in the mechanism/s underlying GTN tolerance and cross-tolerance. According to these reports, increased production of superoxide anion was found to accompany tolerance development to GTN in vascular tissue. Treatment with superoxide dismutase (SOD) significantly enhanced relaxation of control and tolerant vascular tissue to GTN and other exogenous and endogenous vasodilators.

While the precise mechanism for the vasorelaxant effect of GTN is unknown, a consensus exists regarding the primary involvement of cGMP in mediating the nitrate-induced relaxation. However, the roles of sulfhydryl groups [reduced glutathione (GSH) and cysteine (Cys)] and of various enzymes in the bioconversion of GIN and subsequent activation of guanylyl cyclase (GC) leading to relaxation have become increasingly controversial. Cysteine was found to be the specific sulfhydryl required for activation of soluble coronary arterial GC and to be the only one of several sulfhydryl to react non enzymatically with GTN at physiologic pH resulting in formation of S-nitrosocysteine. Since S-nitrosothiols were shown to be potent activators of GC, S-nitrosocysteine/thiols were proposed as the intracellular mediators of organic nitrate-induced vasorelaxation. Additionally, N-acetylcysteine (NAC, an immediate donor of Cys thereby increasing GSH) was reported to potentiate GTN activity in vitro and in vivo. The enhanced reaction of thiols with GTN in plasma and blood versus buffer suggested that activation of GC by GTN may be mediated via extracellular formation of S-nitrosothiol/s. In either case (intra- or extracellular S-nitrosothiol formation), this association between sulfhydryls and GTN activity has long been recognized as evidence for the "thiol depletion hypothesis". However, recent studies by the Applicant and those of Boesgard et al. revealed a dissociation between tissue thiol content (measured as Cys and GSH) and nitrate tolerance in vivo.

In vitro inhibitory studies provide indirect support for the involvement of enzymes m GTN bioactivation [glutathione S-transferase (GST) and cytochrome P-450 (P-450)]. However, in view of several other reports suggesting the lack of any significant role of GST and P-450 in GTN bioactivation, the reduced bioactivation of GTN is unlikely to be the main factor underlying nitrate tolerance in vivo. In fact, reduced cGMP production was also shown to follow exposure of vascular preparation to direct NO-donors, for which no definitive metabolic pathway has been reported.

Furthermore, Applicant has recently presented in vivo evidence excluding the involvement of any particular metabolic pathway since reduced cGMP was also shown to follow treatment with S-alkylating agents in the absence of GTN.

Heart disease is the leading cause of death in Western society and is rapidly approaching this leading position worldwide. Ischemic heart disease is the most common heart disease. For over a century, nitroglycerin and other organic nitrates have been used for the treatment of various types of myocardial ischemia, including acute myocardial infarction (AMI) and as adjuncts in the treatment of other heart diseases (congestive heart failure and resistant hypertension). Chronic prophylaxis and acute treatment are necessary to prevent complications of ischemic heart disease with potential fatal outcomes (~25% death for AMI). Tolerance to the anti-ischemic effect of these drugs is, by far, the most serious drawback of therapy with currently available organic nitrates. The compounds proposed in this application constitute a novel approach to overcome tolerance.

SUMMARY OF THE INVENTION

The present invention provides a compound containing at least one sulfhydryl group and at least one NO donor group, wherein said compound is a) a compound containing one or more sulfhydryl groups linked to at least one aromatic ring or a heteroaromatic ring with a nitrogen in the ring structure, which ring is substituted by one or more substituents bearing a terminal —$ONO_2$ group; b) a 5-membered ring heterocyclic compound containing a sulfur atom and a nitrogen atom, which ring is substituted by one or more substituents bearing a terminal —$ONO_2$ group; c) a 5-membered ring compound containing two conjugate S-atoms, which ring is linked to one or more substituents bearing a terminal —$ONO_2$ group; or d) a compound containing an acyclic —S—S group, linked to at least one aromatic ring or a heteroaromatic ring with a nitrogen in the ring structure, which ring is substituted by one or more substituents bearing a terminal —$ONO_2$ group.

In one embodiment, the compound is:
1
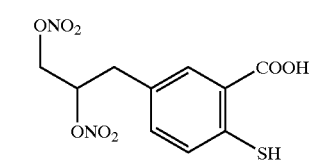
4
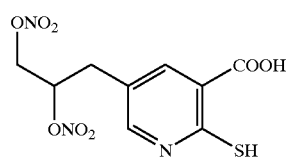
6
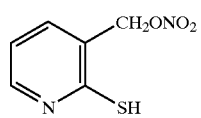
7
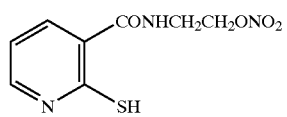
8
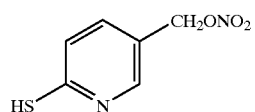
9
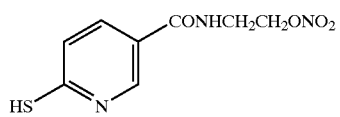
10
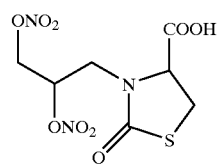
11
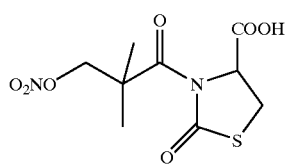
12
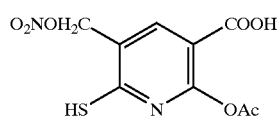
14
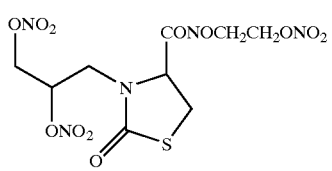
15
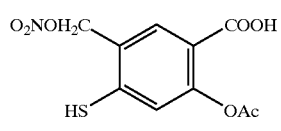
In another embodiment, the compound is:
3
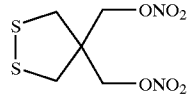
4
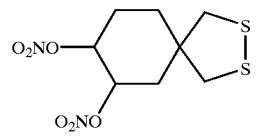
5
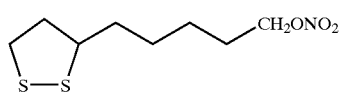
6
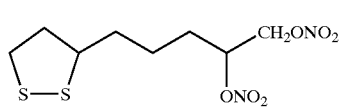
7
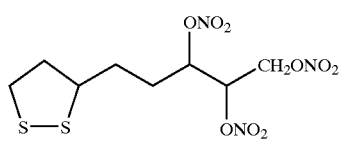
8
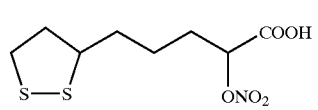
9
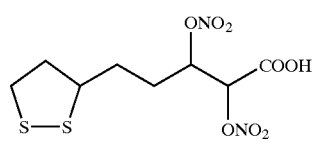
14
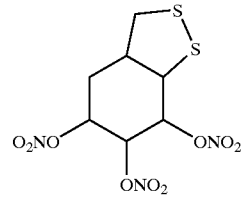
15
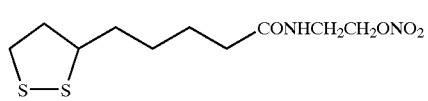
23
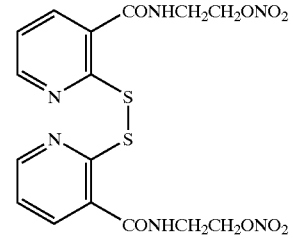

-continued

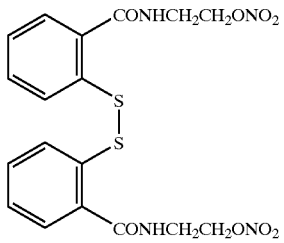
24

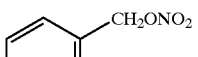

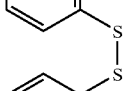
25

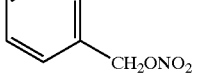
26

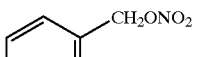

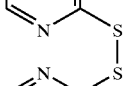
27

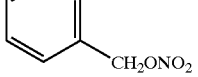
29

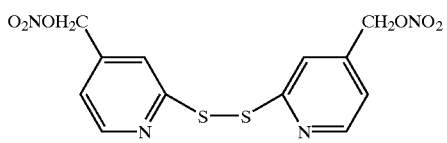
31

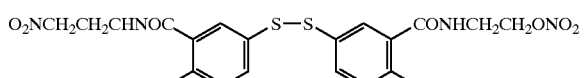

or

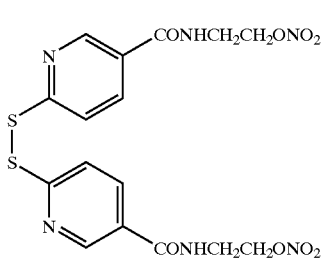
32

The present invention further provides a pharmaceutical composition comprising a) as an active ingredient at least one compound containing at least one sulfhydryl group and at least one NO donor group, wherein said compound is 1) a compound containing one or more sulfhydryl groups linked to at least one aromatic ring or a heteroaromatic ring with a nitrogen in the ring structure, which ring is substituted by one or more substituents bearing a terminal —ONO$_2$ group; 2) a 5-membered ring heterocyclic compound containing a sulfur atom and a nitrogen atom, which ring is substituted by one or more substituents bearing a terminal —ONO$_2$ group; 3) a 5-membered ring compound containing two conjugate S-atoms, which ring is linked to one or more substituents bearing a terminal —ONO$_2$ group; or 4) a compound containing an acyclic —S—S group, linked to at least one aromatic ring or a heteroaromatic ring with a nitrogen in the ring structure, which ring is substituted by one or more substituents bearing a terminal —ONO$_2$ group; and b) a pharmaceutically acceptable carrier.

In one embodiment, the active ingredient is:

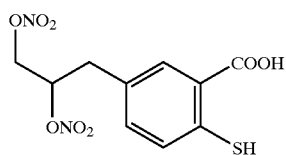
1

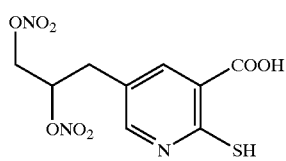
4

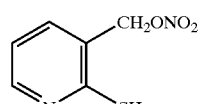
6

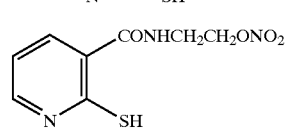
7

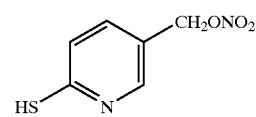
8

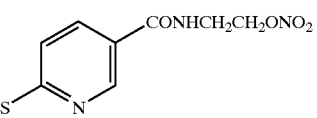
9

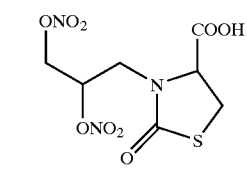
10

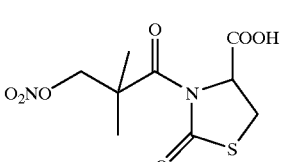
11

-continued
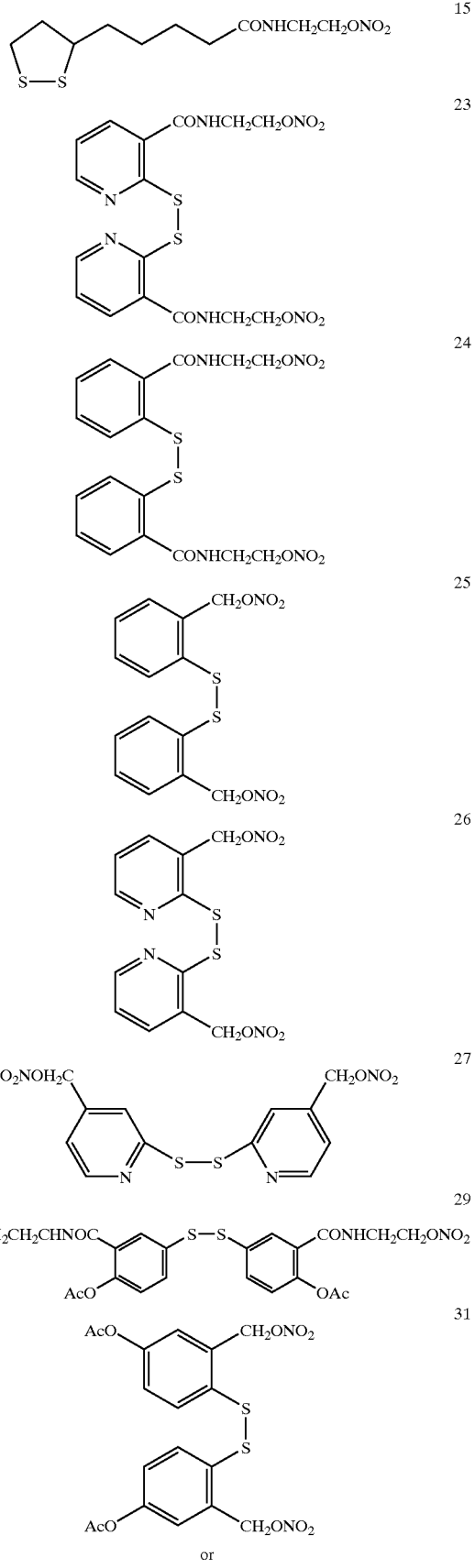
In another embodiment, the active ingredient is:
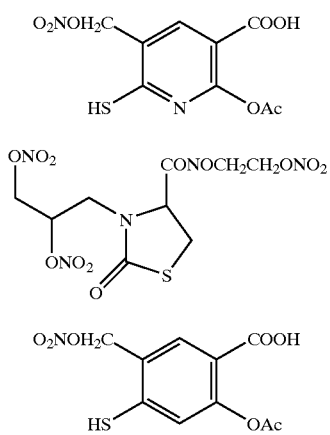

-continued

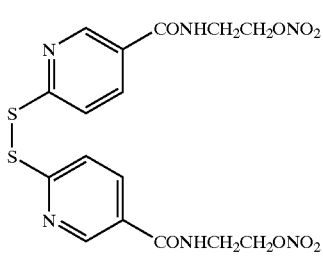

32

DETAILED DESCRIPTION OF THE PRESENT INVENTION

The present invention provides a compound containing at least one sulfhydryl group and at least one NO donor group, wherein said compound is a) a compound containing one or more sulfhydryl groups linked to at least one aromatic ring or a heteroaromatic ring with a nitrogen in the ring structure, which ring is substituted by one or more substituents bearing a terminal —$ONO_2$ group; b) a 5-membered ring heterocyclic compound containing a sulfur atom and a nitrogen atom, which ring is substituted by one or more substituents bearing a terminal —$ONO_2$ group; c) a 5-membered ring compound containing two conjugate S-atoms, which ring is linked to one or more substituents bearing a terminal —$ONO_2$ group; or d) a compound containing an acyclic —S—S group, linked to at least one aromatic ring or a heteroaromatic ring with a nitrogen in the ring structure, which ring is substituted by one or more substituents bearing a terminal —$ONO_2$ group. The present invention further provides pharmaceutical compositions comprising one or more of said compounds as an active ingredient.

The compounds are in vivo nitric oxide donors and they contain at least one sulfhydryl group. As defined herein, a sulfhydryl group is either present in the reduced —SH form, or is a group capable of being converted in-vivo to a sulfhydryl group. In one embodiment, the compounds contain a sulfhydryl group in the reduced —SH form. In another embodiment, the compounds contain a group capable of being converted in-vivo to a sulfhydryl group. Suitable groups which are capable of being converted in-vivo to a sulfhydryl group are illustrated in the following embodiments: In one embodiment, the sulfhydryl group is in the oxidized —S—S disulfide form. In another embodiment, the sulfhydryl is present in a separately protected form (acetyl, carbamyl or other). In another embodiment, the sulfhydryl is present as an atom in a heterocyclic compound. In cases where the compound contains two sulfhydryl groups, these can exist in the reduced (SH) or the oxidized (disulfide) form or in a protected form. However, each one of the compounds can also be regarded as a parent pro-drug which is assumed to undergo metabolic reduction or cleavage to provide the free SH groups in-vivo.

In one embodiment, the compound is a compound containing one or more sulfhydryl groups linked to at least one aromatic ring or a heteroaromatic ring with a nitrogen in the ring structure, which ring is substituted by one or more substituents bearing a terminal —$ONO_2$ group. In another embodiment, the compound is a 5-membered ring heterocyclic compound containing a sulfur atom and a nitrogen atom, which ring is substituted by one or more substituents bearing a terminal —$ONO_2$ group. In another embodiment, the compound is a 5-membered ring compound containing two conjugate S-atoms, which ring is linked to one or more substituents bearing a terminal —$ONO_2$ group. In another embodiment the compound is a compound containing an acyclic —S—S group, linked to at least one aromatic ring or a heteroaromatic ring with a nitrogen in the ring structure, which ring is substituted by one or more substituents bearing a terminal —$ONO_2$ group.

In accordance with an alternative embodiment of the present invention, the compound is a 6-membered ring compound containing two conjugate S-atoms which is substituted by one or more —$ONO_2$ groups or linked to one or more substituents bearing a terminal —$ONO_2$ group. In another embodiment the compound is a 6-membered ring compound containing 2 conjugate S-atoms which is substituted by one or more —$ONO_2$ groups or linked to one or more substituents bearing a terminal —$ONO_2$ group, wherein said 6-membered ring is conjugated to at least one carbocyclic aromatic nucleus or at least one pyridine nucleus. In another embodiment, the compound is a compound having an S—S group in an open configuration linked to one or more —$ONO_2$ groups or linked to one or more substituents bearing a terminal —$ONO_2$ group.

In one embodiment, the compound is:

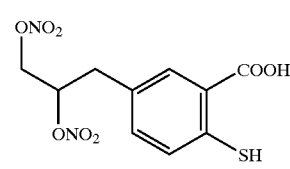

1

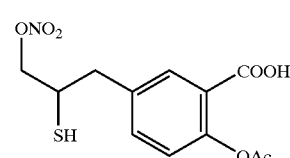

2

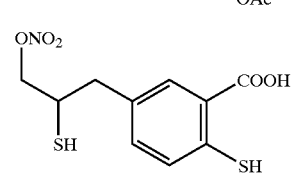

3

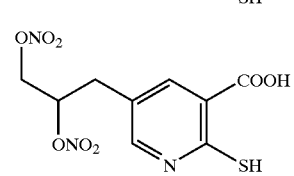

4

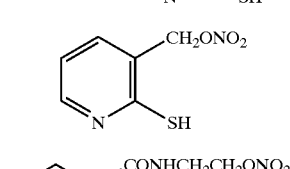

6

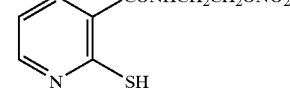

7

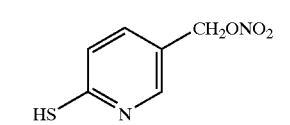

8

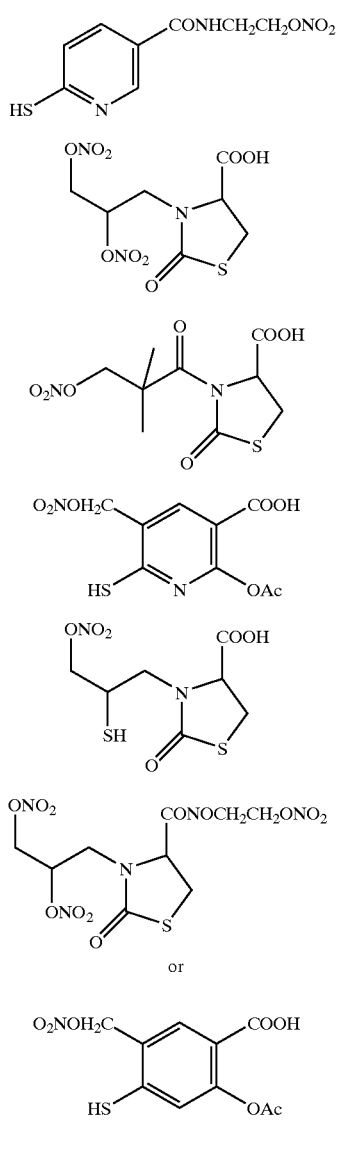
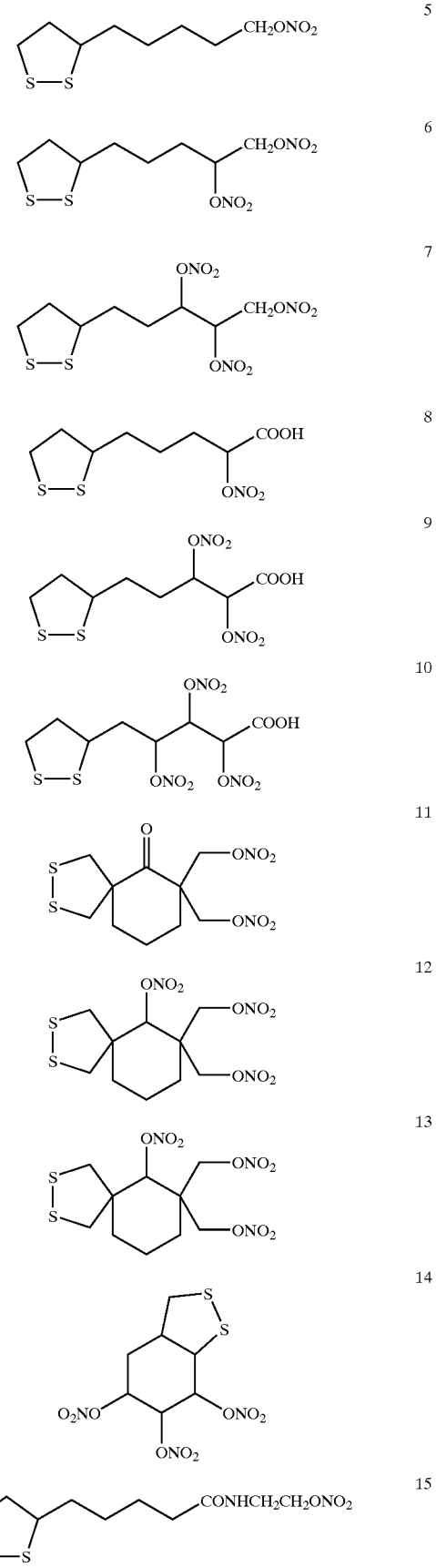
In another embodiment, the compound is:
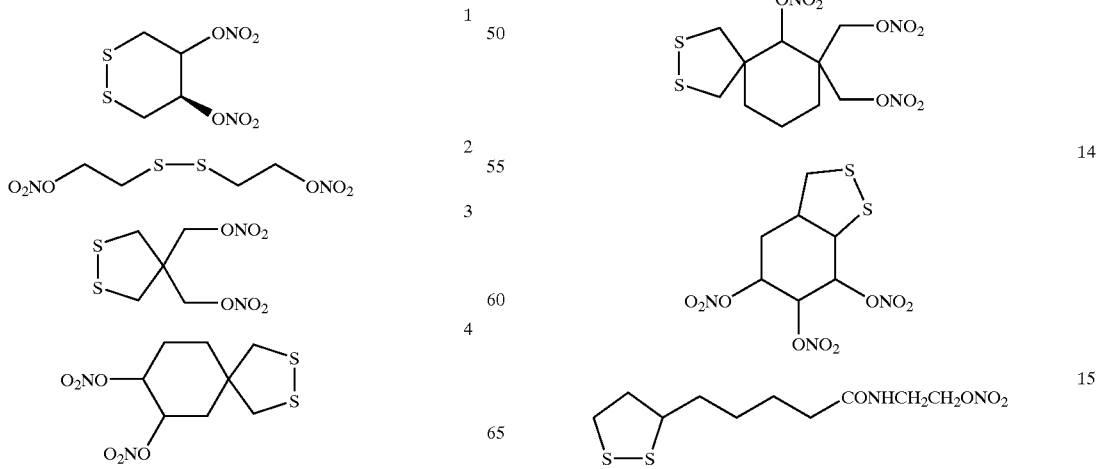

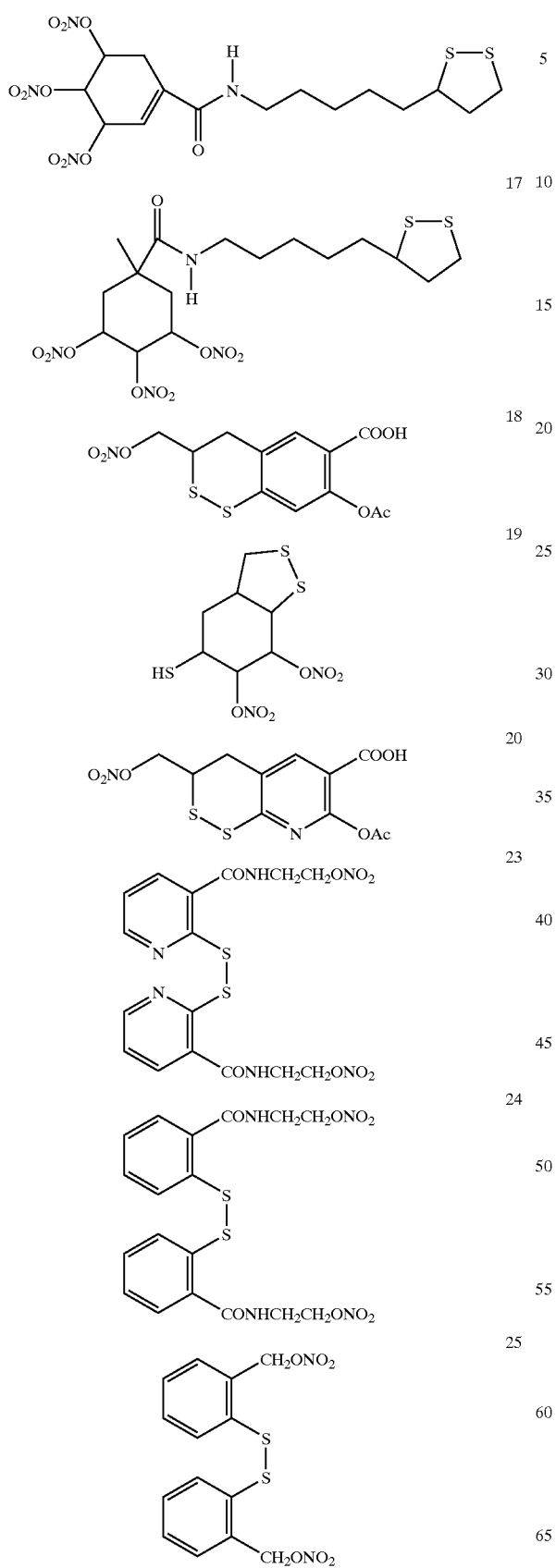
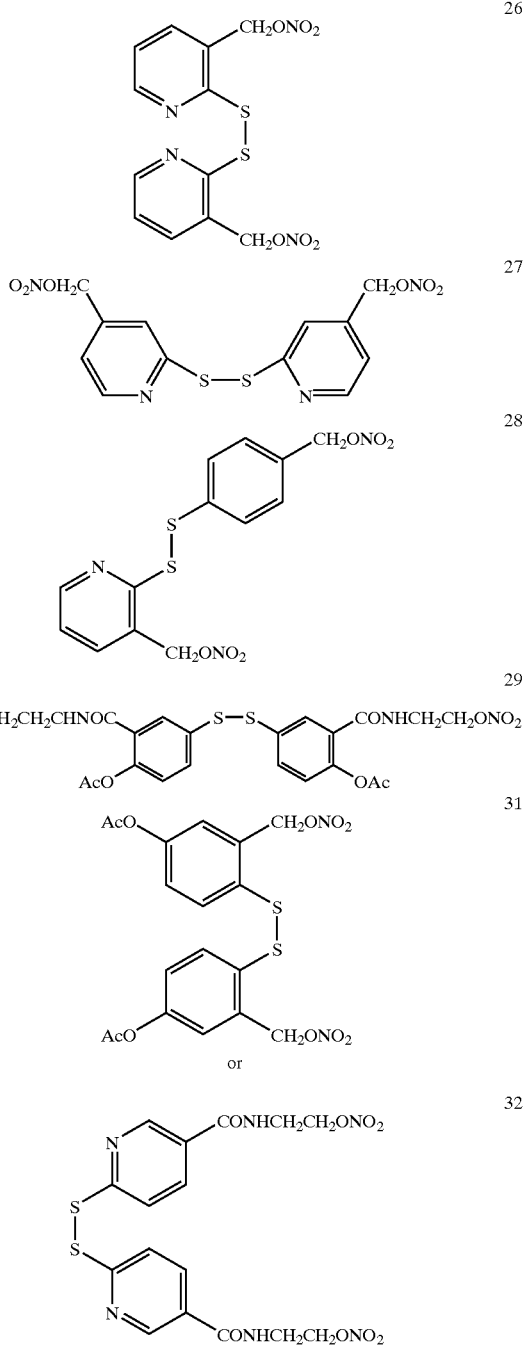

All of the above compounds are such that they will undergo in vivo metabolic cleavage to provide free —SH groups.

According to this invention, whenever a compound exists in the acid form, the term "acid" should also be understood to include the corresponding acid halide, salts with pharmacologically acceptable alkali metal (including alkaline earth metal and ammonium bases), esters and amides. Moreover, the alcohol or the amines used to form the corresponding ester and amides of the acid can also bear a nitrate ester.

The present invention further provides a pharmaceutical composition for the treatment of disorders where nitric oxide donors are indicated, comprising a) as an active ingredient at least one compound containing at least one sulfhydryl group and at least one NO donor group, wherein said compound is 1) a compound containing one or more sulfhydryl groups linked to at least one aromatic ring or a heteroaromatic ring with a nitrogen in the ring structure, which ring is substituted by one or more substituents bearing a terminal —ONO$_2$ group; 2) a 5-membered ring heterocyclic compound containing a sulfur atom and a nitrogen atom, which ring is substituted by one or more substituents bearing a terminal —ONO$_2$ group; 3) a 5-membered ring compound containing two conjugate S-atoms, which ring is linked to one or more substituents bearing a terminal —ONO$_2$ group; or 4) a compound containing an acyclic —S—S group, linked to at least one aromatic ring or a heteroaromatic ring with a nitrogen in the ring structure, which ring is substituted by one or more substituents bearing a terminal —ONO$_2$ group; and b) a pharmaceutically acceptable carrier.

In one embodiment, the active ingredient is a compound containing one or more sulfhydryl groups linked to at least one aromatic ring or a heteroaromatic ring with a nitrogen in the ring structure, which ring is substituted by one or more substituents bearing a terminal —ONO$_2$ group. In another embodiment, the active ingredient is a 5-membered ring heterocyclic compound containing a sulfur atom and a nitrogen atom, which ring is substituted by one or more substituents bearing a terminal —ONO$_2$ group. In another embodiment, the active ingredient is a 5-membered ring compound containing two conjugate S-atoms, which ring is linked to one or more substituents bearing a terminal —ONO$_2$ group. In another embodiment the active ingredient is a compound containing an acyclic —S—S group, linked to at least one aromatic ring or a heteroaromatic ring with a nitrogen in the ring structure, which ring is substituted by one or more substituents bearing a terminal —ONO$_2$ group.

In accordance with an alternative embodiment, the active ingredient is a 6-membered ring compound containing two conjugate S-atoms which is substituted by one or more —ONO$_2$ groups or linked to one or more substituents bearing a terminal —ONO$_2$ group. In another embodiment the active ingredient is a 6-membered ring compound containing 2 conjugate S-atoms which is substituted by one or more —ONO$_2$ groups or linked to one or more substituents bearing a terminal —ONO$_2$ group, wherein said 6-membered ring is conjugated to at least one carbocyclic aromatic nucleus or at least one pyridine nucleus.

In another embodiment, the active ingredient is a compound having an S—S group in an open configuration linked to one or more —ONO$_2$ groups or linked to one or more substituents bearing a terminal —ONO$_2$ group.

In one embodiment, the active ingredient is

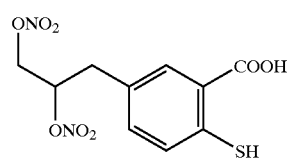

1

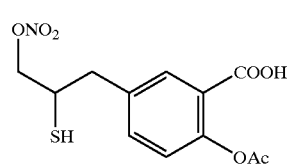

2

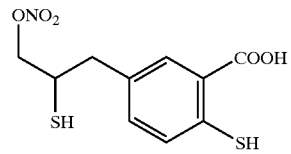

3

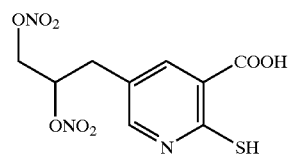

4

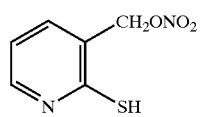

6

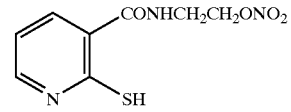

7

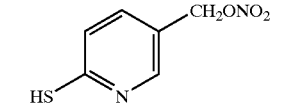

8

9

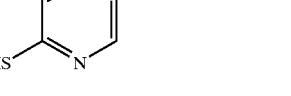

10

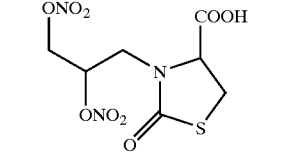

11

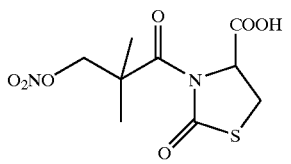

12

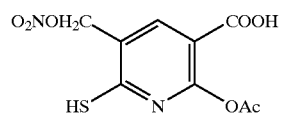

13

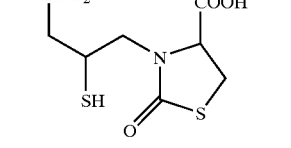

14

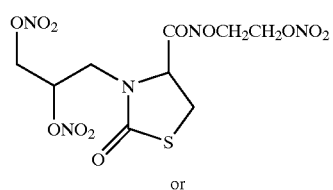

or

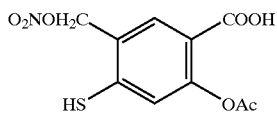
In another embodiment, the active ingredient is:
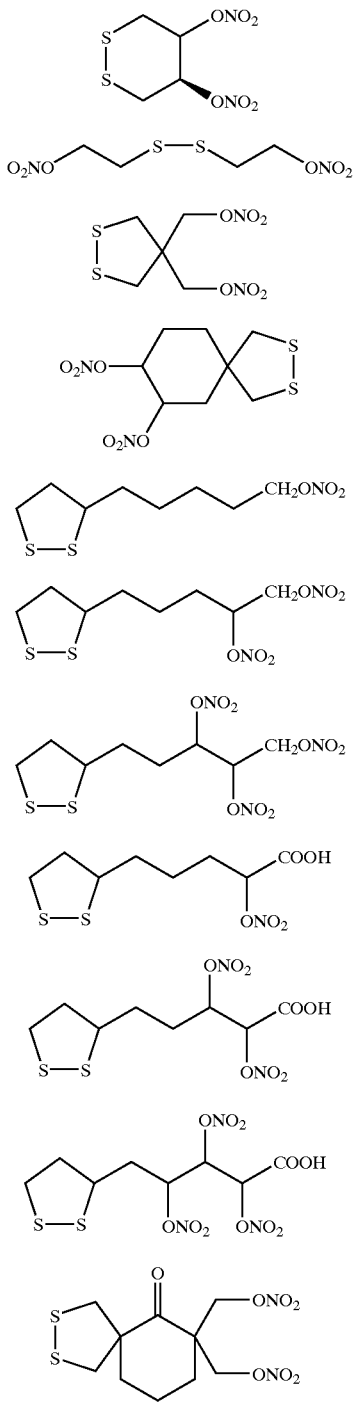
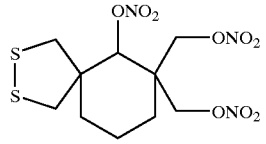
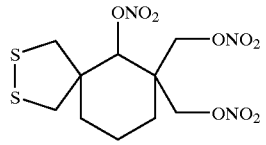
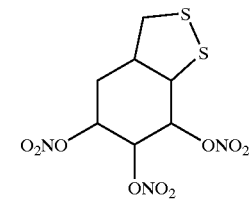
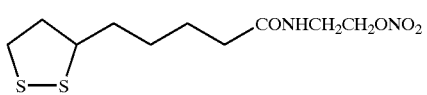
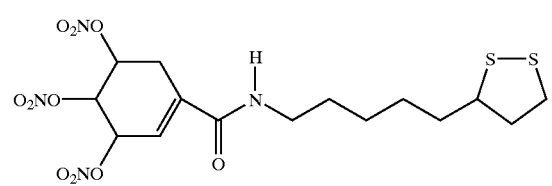
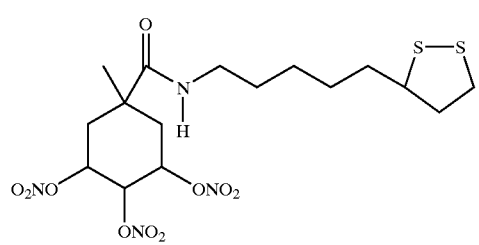
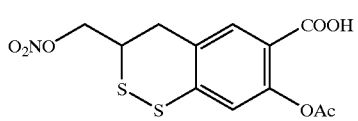
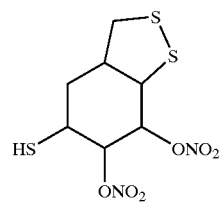
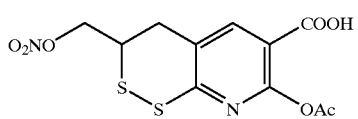

23 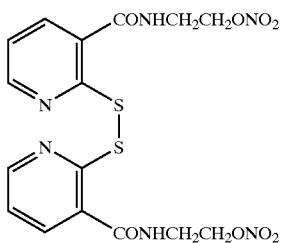

24 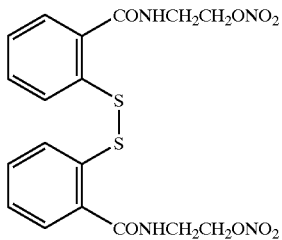

25 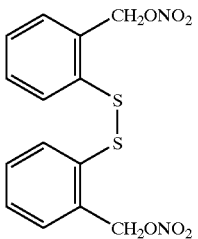

26 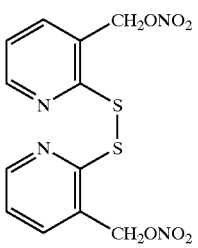

27 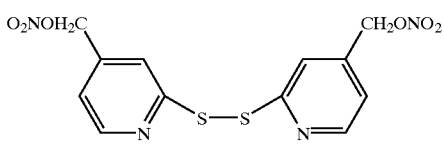

28 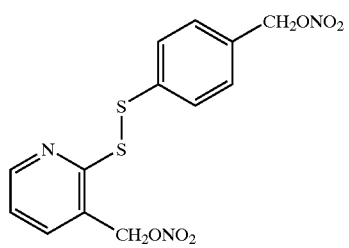

29 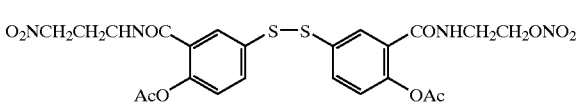

31 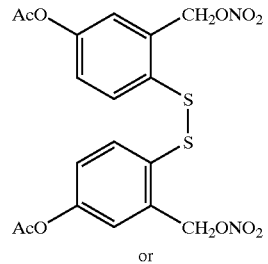

or

32 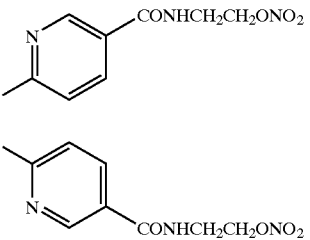

Because of their SH-content (radical scavenging and anti-oxidant properties), these compounds may also be applied for other pathologies. Thus, considering their promising chemical and pharmacological characteristics and the ever-increasing demand for better therapy for heart diseases, significant potential exists for compounds of this type to become the next generation of vasodilators. This is especially true concerning the considerable amount of recent evidence indicating the involvement of nitric oxide, reactive oxygen species and thiols in a variety of conditions, the pathogenesis of as well as the treatment for which have not been fully resolved. These include (but are not limited to): atherosclerosis, pulmonary and systemic hypertension, asthma and other related respiratory diseases, trauma, shock, neurotoxicity, neurodegenerative and neurologic disorders, including those involving learning, memory, olfaction and nociception, Huntington, Alzheimer and Parkinson's diseases, multiple sclerosis and convulsive (seizure) disorders, AIDS-related disorders (i.e. dementia), disorders of gastric acid and other secretory and peristaltic functions of the alimentary system, drug and disease-induced neuropathy and nephropathy, pathological and premature uterine contractions, cellular defense impairment, and insulin-resistance in glucose intolerance and diabetes mellitus, pregnancy-induced hypertension, chemotaxis and phagocytic impairment in immunological disorders, cerebrovascular diseases, aggregation disorders, perile erection and treatment of male impotence.

Although the exact mechanisms defining organic nitrates and other nitric oxide donors' action and tolerance are not completely elucidated, the primary roles of nitric oxide (being their first messenger) and cGMP (the second messenger) in mediating vasorelaxation are universally accepted. Applicant has demonstrated herein, utilizing example compounds 1 to 6 from page 14, that, unlike currently available organic and inorganic nitrates, these compounds possess equipotent or ever superior vasorelaxant activity. Moreover, using cGMP measurements both in extended periods of exposure to the drug when used, for example, in nitroglycerin-equimolar dosing regimens for which tolerance to the cGMP-inducing activity of nitroglycerin has been documented under the same experimental conditions (see table on page 30).

For the preparation of pharmaceutical compositions, the novel compounds are mixed in the usual way with appropriate pharmaceutical carrier substances, aroma, flavoring and coloring materials and formed, for example, into tablets or dragees of immediate or sustained release or, with additions of appropriate adjuvants, for example water or an oil such as olive or other oil, are suspended or dispersed or dissolved.

The compounds or the pharmaceutical composition thereof can be administered orally (including the sublingual and buccal routes) or via an injectable form (including the subcutaneous, intramuscular, intraperitoneal and the parenteral routes). Other routes of administration such as aerosols and dermal preparations are also to be considered. As injection medium, water is preferably used which contains the stabilizing agents, solubilizing agents and/or buffers usually utilized in the preparation of solutions for injection. Such additives include, for example, tartarate and borate buffers, ethanol, ethylene and propylene glycols, glycerol, dimethyl sulphoxide, complex formers (i.e., ethylenediamine tetraacetic acid), high molecular weight polymers (such as liquid polyethylene oxide) for viscosity regulation and polyethylene derivatives of sorbit anhydrides. Solid carrier materials include, for example, starch, lactose, manitol, methyl cellulose, talc, highly dispersed silicic acid, high molecular weight polymers (i.e., polyethylene glycol). Compositions suitable for oral administration (as defined above) can, if necessary, contain flavoring and sweetening agents.

The synthesis of the novel compounds was carried out utilizing conventional organic synthetic methods. The following examples are given for the purpose of illustrating the present invention:

EXAMPLE 1 trans-1,2-Dinitrato-4,5-dithiane (Compound 1. Page 14)

The compound was easily synthesized utilizing the commercially available precursor trans-1,2-dihydroxy-4,5-dithiane. 0.5 g of the precursor was added portionwise to chilled (−5° C.) 1:1 mixture of fuming nitric sulfuric acids. Upon completion of the addition, the ice/salt bath was removed and the mixture brought to room temperature. This mixture was added dropwise to a cooled mixture of dry diethyl ether:acetonitrile:water (70:20:10) with vigorous stirring. The lower aqueous phase was separated and extracted twice with diethyl ether. The combined organic extracts were washed twice with water and once with cold 1% sodium carbonate solution. The organic layer was dried over magnesium sulfate and evaporated to near dryness under reduced pressure. The residual oil was loaded on a silica column and separated after elution with hexane. Evaporation under reduced pressure of the eluate yielded a yellowish oil (0.56 g) with analytical data consistent with the structure of trans-1,2-dinitrato4,5-dithiane.

EXAMPLE 2

2,2'-Dithiodiethanol-dinitrate (Compound 2, Page 14)

The compound was synthesized in a similar fashion to compound 1 above using the commercially available precursor 2,2'-dithiodiethanol as the starting material. The precursor was nitrated and separated as above yielding the title compound 2,2'-dithiodiethanol-dinitrate.

EXAMPLE 3

1,1-Diemethanol-dinitrate-3,4-dithiane (Compound 3, Page 14)

This compound was synthesized by bishydroxymethylation of diethyl malonate followed by thiolation of the hydroxyl groups (via the halide intermediate). The resulting 1,1-dicarboxy-3,4-dithiane was reduced by borane (catechol borane solution) to the corresponding 1,1-diemethanol-3,4-dithiane. Direct nitration of this latter intermediate yielded the title compound 1,1-diemethanol initrate-3,4-dithiane.

EXAMPLE 4

1,1'-Bisthiomethyl-3,4-dihydroxy-cyclohexane-dinitrate ester (Compound 4, Page 14)

This compound was synthesized by thiolation of the dichloride intermediate of the commercially available 1,1'-bishydroxymethyl-3-cyclohexene. Oxidation of the double bond either by hydrogen peroxide/asmium tetroxide to generate the cis-diol or by a peracid/formic acid mixture to generate the trans-diol followed by nitration of the diol will generate the corresponding (cis or trans) form of the title compound.

EXAMPLE 5

Thioctyl Alcohol Nitrate Ester (Compound 5, Page 14)

This compound was synthesized in a high yield process utilizing Thioctyl acid as the precursor. Following reduction of the acid (or its methyl or ethyl ester) by catechol borane solution, the resulting thioctyl alcohol was separated and mitrated as described above to yield the title compound.

EXAMPLE 6

1,2-Dihydroxy-dinitrate-6,8-dithiane (Compound 6, Page 14)

2-Hydroxy lipoic (thioctic) acid was synthesized from thioctic acid via the 2-bromo derivative. This intermediate was reduced via borane to yield the direct precursor 1,2-dihydroxy-6,8-dithiane which, upon nitration as described above, yielded the title compound.

Experimental Report

Representative for the new compounds, the vasorelaxant activities (measured as the ability of the tested drug to induce an increase in vascular cGMP) of the example compounds 1 to 6 were determined and compared to activity of nitroglycerin under the same experimental conditions following single and sustained exposure of rats to the compound.

For this purpose the compound to be tested was administered, in each case, to 8 male Sprague-Dawley rats (300–400 g) before and after an 18 hr continuous intravenous infusion of the compound. The 18 hr continuous infusion period was determined based on existing data demonstrating the development of tolerance to the drug effect in the case of nitroglycerin. The existence of tolerance to the drug is demonstrated by the inability of the drug to attain 50% or more of the cGMP values measured in the vascular tissue after dosing of the drug to preciously treated animals as compared to controls (non-treated or vehicle-treated animals). After drug administration (i.v. push), the rat was sacrificed, the aorta immediately removed and processed for cGMP measurement as has been described in detail by us. All of the tested new compounds were utilized in nitroglycerin equimolar doses, either before of after the "tolerance" induction period.

The following table summarizes the results obtained following administration of either nitroglycerin or the tested compounds before and after an 18 hr continuous exposure to the same compound:

|  | cGMP (pmol/g tissue) | |
| --- | --- | --- |
| Tested Compound | Pre-infusion | Post-infusion |
| Nitroglycerin | 153 ± 13 | 68 ± 9** |
| Compound 1 | 196 ± 14 | 189 ± 13* |
| Compound 2 | 169 ± 12 | 174 ± 13* |
| Compound 3 | 171 ± 14 | 174 ± 16* |
| Compound 4 | 149 ± 11 | 169 ± 13* |
| Compound 5 | 123 ± 13 | 113 ± 11* |
| Compound 6 | 193 ± 17 | 179 ± 12* |

**Significantly different from the pre-infusion values and denotes tolerance.
*Not significantly different from pre-infusion levels and denotes the lack of tolerance.

Besides their expected superior vasorelaxant activity, these results clearly demonstrate that whereas tolerance to the cGMP-inducing activity of nitroglycerin developed early (18 hr) following its continuous in vivo administration, no tolerance was observed to the cGMP-increasing effects of the novel compounds under the same experimental conditions used for the induction of in vivo tolerance. In fact, Applicant shows in preliminary results that no tolerance to this cGMP-inducing effect of these novel SH-containing-NO-donors develops even after exposure of the animals to the compounds for extended periods of time (i.e., not even after 168 hr of continuous intravenous infusions).

It will be understood that the compounds shown demonstrate the principle upon which this invention is based. Thus, the specification and examples given in this application are illustrative but not limitative of the present invention and embodiments within the spirit and scope of the invention will suggest themselves to those skilled in the art. Rather, the scope of the invention is defined by the claims which follow.

What is claimed is:

1. A compound containing at least one sulfhydryl group and at least one NO donor group, wherein said compound is:
   - a compound containing one or more sulfhydryl groups linked to at least one aromatic ring or a heteroaromatic ring with a nitrogen in the ring structure, which ring is substituted by one or more substituents bearing a terminal —$ONO_2$ group;
   - a 5-membered ring heterocyclic compound containing a sulfur atom and a nitrogen atom, which ring is substituted by one or more substituents bearing a terminal —$ONO_2$ group;
   - a 5-membered ring compound containing two conjugate S-atoms, which ring is linked to one or more substituents bearing a terminal —$ONO_2$ group; or
   - a compound containing an acyclic —S—S group, linked to at least one aromatic ring or a heteroaromatic ring with a nitrogen in the ring structure, which ring is substituted by one or more substituents bearing a terminal —$ONO_2$ group.

2. A compound according to claim 1, wherein said compound is:

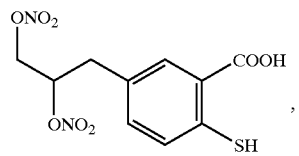

,

-continued

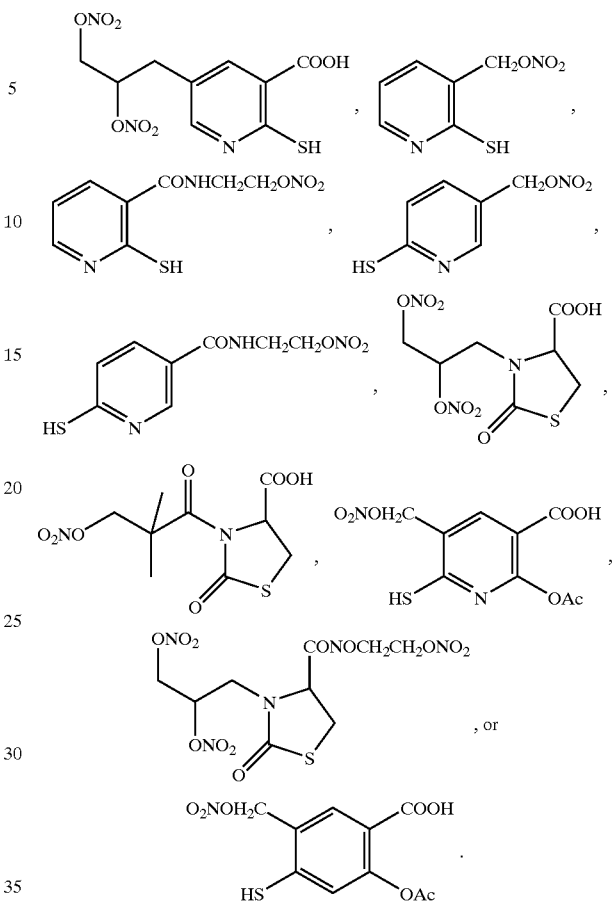

3. A compound according to claim 1, wherein said compound is:

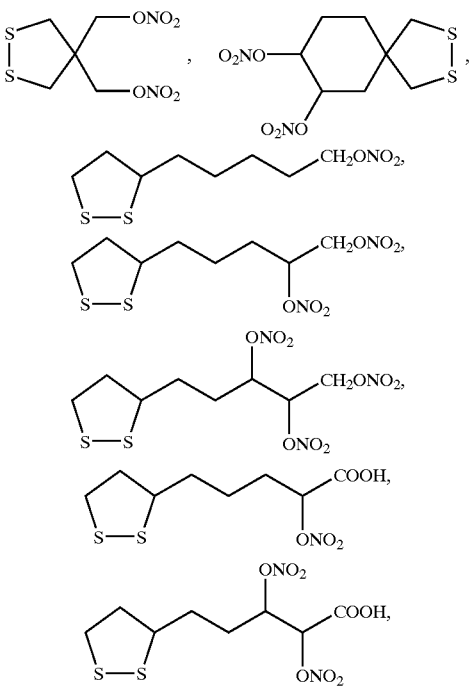

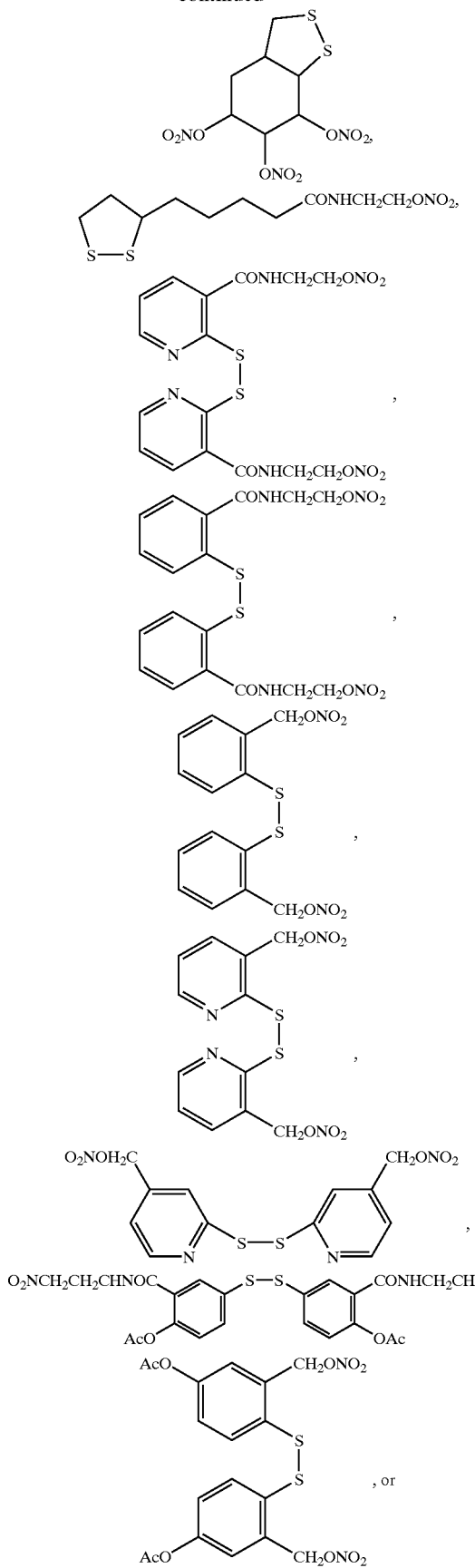

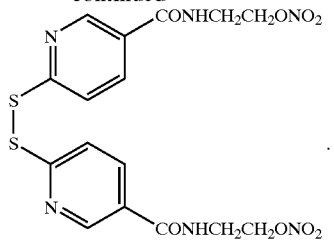

4. A pharmaceutical composition comprising
a) as an active ingredient at least one compound containing at least one sulfhydryl group and at least one NO donor group, wherein said compound is:
  a compound containing one or more sulfhydryl groups linked to at least one aromatic ring or a heteroaromatic ring with a nitrogen in the ring structure, which ring is substituted by one or more substituents bearing a terminal —$ONO_2$ group;
  a 5-membered ring heterocyclic compound containing a sulfur atom and a nitrogen atom, which ring is substituted by one or more substituents bearing a terminal —$ONO_2$ group;
  a 5-membered ring compound containing two conjugate S-atoms, which ring is linked to one or more substituents bearing a terminal —$ONO_2$ group; or
  a compound containing an acyclic —S—S group, linked to at least one aromatic ring or a heteroaromatic ring with a nitrogen in the ring structure, which ring is substituted by one or more substituents bearing a terminal —$ONO_2$ group; and
b) a pharmaceutically acceptable carrier.

5. A composition according to claim 4 wherein the active ingredient is:

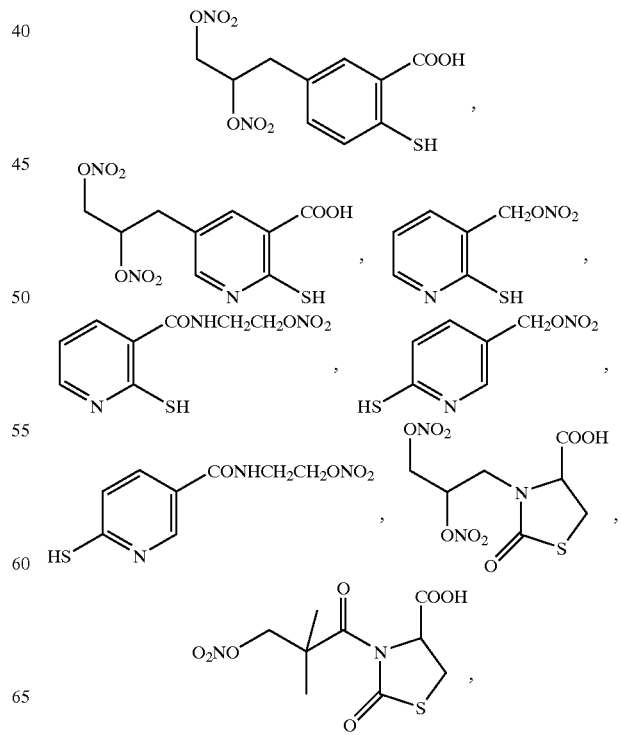

-continued
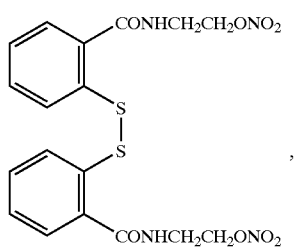
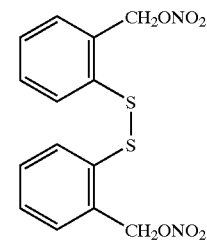
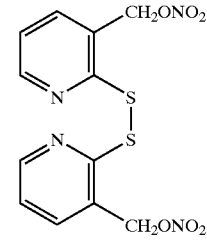
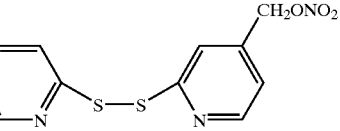
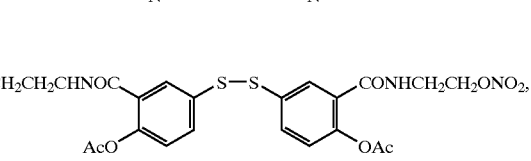
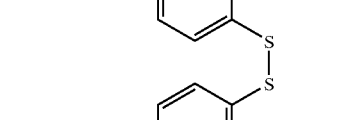
, or
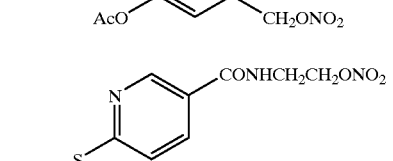
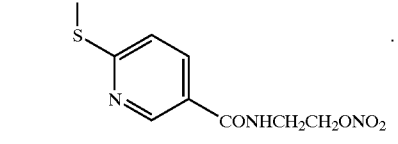
* * * * *
-continued
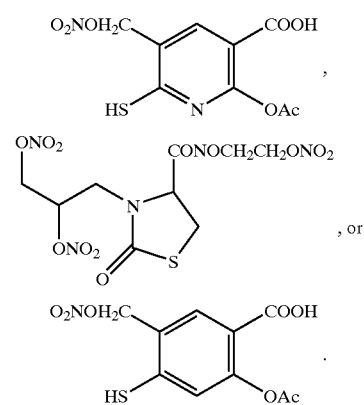
, or
6. A composition according to claim 4, wherein the active ingredient is:
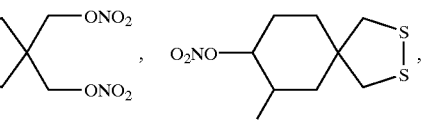
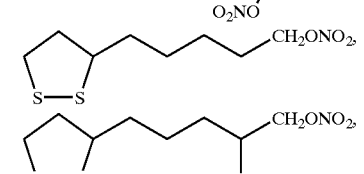
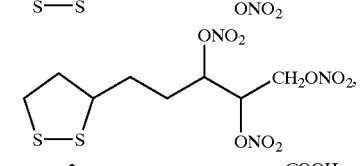
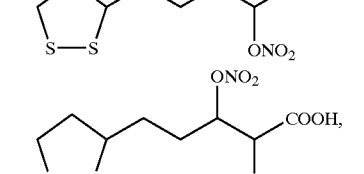
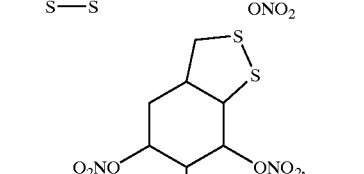
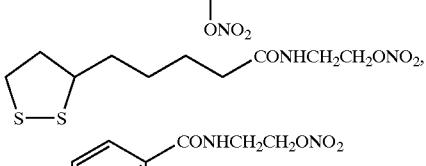
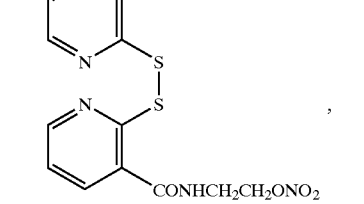
,